US007049143B2

(12) United States Patent
Kim et al.

(10) Patent No.: US 7,049,143 B2
(45) Date of Patent: May 23, 2006

(54) HIGH EFFICIENCY RETROVIRAL VECTOR WHICH CONTAINS GENETICALLY ENGINEERED CELLULAR NON-CODING SEQUENCE HARBORING SPLICING ACCEPTOR

(75) Inventors: Sun-Young Kim, Seoul (KR); Seung-Shin Yu, Seoul (KR); Jun-Tae Lee, Kunsan-si (KR)

(73) Assignee: ViroMed Co., Ltd. (KR)

( * ) Notice: Subject to any disclaimer, the term of this patent is extended or adjusted under 35 U.S.C. 154(b) by 388 days.

(21) Appl. No.: 10/129,422

(22) PCT Filed: Sep. 8, 2001

(86) PCT No.: PCT/KR01/01515

§ 371 (c)(1),
(2), (4) Date: May 1, 2002

(87) PCT Pub. No.: WO02/20810

PCT Pub. Date: Mar. 14, 2002

(65) Prior Publication Data
US 2003/0166251 A1    Sep. 4, 2003

(30) Foreign Application Priority Data
Sep. 8, 2000    (KR) .................... 10-2000-0053613

(51) Int. Cl.
*C12N 5/10* (2006.01)
*C12N 1/21* (2006.01)
*C12N 15/867* (2006.01)
*C12N 15/63* (2006.01)

(52) U.S. Cl. .................. 435/456; 435/320.1; 435/325; 435/455; 435/252.3

(58) Field of Classification Search ............. 435/320.1, 435/235.1, 325, 366, 455, 456, 354, 357, 435/243, 252.3, 252.33; 424/93.1, 93.2, 424/93.6
See application file for complete search history.

(56) References Cited

U.S. PATENT DOCUMENTS
5,693,508 A    12/1997  Chang

FOREIGN PATENT DOCUMENTS
KR    2000-0006334    1/2000
WO    WO 00/00629 A1    1/2000

OTHER PUBLICATIONS

Anderson, Nature, 1998, vol. 392, pp. 25-30.*
Kmeic, American Scientist, 1999, vol. 87, pp. 240-247.*
Fox, Nature Biotechnology, 2000, vol. 18, pp. 143-144.*
Mountain, TIBTECH, 2000, vol. 18, pp. 119-128.*
Juengst, BMJ, 2003, vol. 326, pp. 1410-1411.*
Brenner et al., Biochimica et Biophysica Acta, 2003, vol. 1640, pp. 1-24.*
Marshall, Science, 2003, vol. 299, p. 320.*
Bakker, A.C., et al., "Prevention of Murine Collagen-induced Arthritis in the Knee and Ipsilateral Paw by Local Expression of Human Interleukin-1 Receptor Antagonist Protein in the Knee," *Arth. & Rheum.* 40:893-900, Lippincott, Williams & Wilkins (1997).
Byun, J., et al., "Analysis of the relative level of gene expression from different retroviral vectors used for gene therapy," *Gene. Ther.* 3:780-788, Stockton Press (1996).
Deonarain, M.P., "Ligand-targeted receptor-mediated vectors for gene delivery," *Exp. Opin. Ther. Patents* 8 :53-69, Ashley Publications Ltd. (1998).
Eck, S.L. and Wilson, J.M., "Chapter 5. Gene-Based Therapy," in: Goodman & Gilman's the Pharmacological Basis of Therapeutics, 9th Ed., McGraw-Hill, New York, NY, pp. 77-101 (1996).
Evans, C.H., et al., "Clinical Trial to Assess the Safety, Feasibility, and Efficacy of Transferring a Potentially Anti-Arthritic Cytokine Gene to Human Joints with Rheumatoid Arthritis," *Human Gene Ther.* 7:1261-1280, Mary Ann Liebert, Inc. (1996).
Górecki, D.C., "Prospects and problems of gene therapy: an update," *Expert Opin. Emerging Drugs* 6:187-198, Ashley Publications Ltd. (Oct. 2001).
Kim, S.H., et al., "Construction of Retroviral Vectors with Improved Safety, Gene Expression, and Versatility," *J. Virol.* 72:994-1004, American Society for Microbiology (1998).
Lee, J.T., et al., "Engineering the splice acceptor for improved gene expression and viral titer in an MLV-based retroviral vector," *Gene Ther.* 11:94-99, Nature Publishing Group (Jan. 2004).
Nouvel, P., et al., "The Spread of a Replication-Competent MuLV Retroviral Vector Can Be Efficiently Blocked by Deletion Variants," *Virol.* 204:180-189, Academic Press, Inc. (1994).
Pfeifer A. and Verma, I.M. "Chapter 13. Virus Vectors and Their Applications," in: *Goodman & Gilman's The Pharmacological Basis of Therapeutics*, 9th Ed., McGraw-Hill, New York, NY, pp. 353-355 (1996).
Robbins, P.D., et al., "Gene therapy for arthritis," *Gene Therapy 10*:902-911, Nature Publishing Group (May 2003).
Verma, I.M. and Somia, N., "Gene therapy—promises, problems and prospects," *Nature 389*:239-242, Nature Publishing Group (1997).
Yu, S.S., et al., "High efficiency retroviral vectors that contain no viral coding sequences," *Gene Ther.* 7:797-804, Macmillian Publishers Ltd. (May 2000).

* cited by examiner

*Primary Examiner*—David Guzo
(74) *Attorney, Agent, or Firm*—Sterne, Kessler, Goldstein & Fox P.L.L.C.

(57) ABSTRACT

The present invention provides a safe and highly efficient retroviral vector derived from the MLV (murine leukemia virus) for use in gene therapy, which lacks viral coding sequences but contains the genetically engineered EF Iα non-coding sequence harboring splicing acceptor.

29 Claims, 10 Drawing Sheets

SEQUENCE LISTING

```
<160> NUMBER OF SEQ ID NOS: 15

<210> SEQ ID NO 1
<211> LENGTH: 234
<212> TYPE: DNA
<213> ORGANISM: Homo sapiens
<220> FEATURE:
<221> NAME/KEY: intron
<222> LOCATION: (1)..(204)
<223> OTHER INFORMATION: intron of human elongation factor 1-alpha gene
      (corresponding to the sequence of +773-+976)
<220> FEATURE:
<221> NAME/KEY: exon
<222> LOCATION: (205)..(234)
<223> OTHER INFORMATION: exon 2 of human elongation factor 1-alpha gene
      which ends just before the stop codon for translation
      (corresponding to the sequence of +977-+1008)

<400> SEQUENCE: 1
tcgagctttt ggagtacgtc gtctttaggt tgggggagg ggttttatgc gatggagttt        60
ccccacactg agtgggtgga gactgaagtt aggccagctt ggcacttgat gtaattctcc      120
ttggaatttg ccctttttga gtttggatct tggttcattc tcaagcctca gacagtggtt      180
caaagttttt ttcttccatt tcaggtgtcg tgaaaactac ccctaaaagc caaa            234

<210> SEQ ID NO 2
<211> LENGTH: 38
<212> TYPE: DNA
<213> ORGANISM: Artificial Sequence
```

-continued

<220> FEATURE:
<223> OTHER INFORMATION: primer EI5'

<400> SEQUENCE: 2
acgcgtgtcg agcttttgga gtacgtcgtc tttaggtt                38

<210> SEQ ID NO 3
<211> LENGTH: 42
<212> TYPE: DNA
<213> ORGANISM: Artificial Sequence
<220> FEATURE:
<223> OTHER INFORMATION: primer EI3'-1s

<400> SEQUENCE: 3
ggatccgttt aaacacctga aatggaagaa aaaaactttg aa           42

<210> SEQ ID NO 4
<211> LENGTH: 42
<212> TYPE: DNA
<213> ORGANISM: Artificial Sequence
<220> FEATURE:
<223> OTHER INFORMATION: primer EI3'-2s

<400> SEQUENCE: 4
ggatccgttt aaacgcctga aatggaagaa aaaaactttg aa           42

<210> SEQ ID NO 5
<211> LENGTH: 38
<212> TYPE: DNA
<213> ORGANISM: Artificial Sequence
<220> FEATURE:
<223> OTHER INFORMATION: primer EI5'm

<400> SEQUENCE: 5
acgcgtgtcg agcttttgga gtactgcgtc tttaggtt                38

<210> SEQ ID NO 6
<211> LENGTH: 42
<212> TYPE: DNA
<213> ORGANISM: Artificial Sequence
<220> FEATURE:
<223> OTHER INFORMATION: EI3'-1l

<400> SEQUENCE: 6
tttttggctt ttaggggtag ttttcacgac acctgaaatg ga           42

<210> SEQ ID NO 7
<211> LENGTH: 42
<212> TYPE: DNA
<213> ORGANISM: Artificial Sequence
<220> FEATURE:
<223> OTHER INFORMATION: primer EI3'-2l

<400> SEQUENCE: 7
tttttggctt ttaggggtag ttttcacgac ggctgaaatg ga           42

<210> SEQ ID NO 8
<211> LENGTH: 42
<212> TYPE: DNA
<213> ORGANISM: Artificial Sequence
<220> FEATURE:
<223> OTHER INFORMATION: primer Luc5'

<400> SEQUENCE: 8
ggatccatgg aagacgccaa aaacataaag aaaggcccgg cg           42

```
<210> SEQ ID NO 9
<211> LENGTH: 35
<212> TYPE: DNA
<213> ORGANISM: Artificial Sequence
<220> FEATURE:
<223> OTHER INFORMATION: primer Luc3'

<400> SEQUENCE: 9
agatctacaa tttggacttt ccgcccttct tggcc                          35

<210> SEQ ID NO 10
<211> LENGTH: 36
<212> TYPE: DNA
<213> ORGANISM: Artificial Sequence
<220> FEATURE:
<223> OTHER INFORMATION: primer IRAP5'

<400> SEQUENCE: 10
ggatccatgg aaatctgcag aggcctccgc agtcac                         36

<210> SEQ ID NO 11
<211> LENGTH: 36
<212> TYPE: DNA
<213> ORGANISM: Artificial Sequence
<220> FEATURE:
<223> OTHER INFORMATION: primer IRAP3'

<400> SEQUENCE: 11
agatctctac tcgtcctcct ggaagtagaa tttggt                         36

<210> SEQ ID NO 12
<211> LENGTH: 33
<212> TYPE: DNA
<213> ORGANISM: Artificial Sequence
<220> FEATURE:
<223> OTHER INFORMATION: sense primer for PCR of IRES gene

<400> SEQUENCE: 12
ggatccgcgg ccgcgaattc cgcccctctc cct                            33

<210> SEQ ID NO 13
<211> LENGTH: 42
<212> TYPE: DNA
<213> ORGANISM: Artificial Sequence
<220> FEATURE:
<223> OTHER INFORMATION: antisense primer for PCR of IRES gene

<400> SEQUENCE: 13
agatctatcg ataggcctca tggttgtggc catattatca tc                  42

<210> SEQ ID NO 14
<211> LENGTH: 32
<212> TYPE: DNA
<213> ORGANISM: Artificial Sequence
<220> FEATURE:
<223> OTHER INFORMATION: sense primer for PCR of MDR gene

<400> SEQUENCE: 14
ggatccatcg atatggatct tgaaggggac cg                             32

<210> SEQ ID NO 15
<211> LENGTH: 32
<212> TYPE: DNA
<213> ORGANISM: Artificial Sequence
<220> FEATURE:
<223> OTHER INFORMATION: antisense primer for PCR of MDR gene
```

```
<400> SEQUENCE: 15
ggatccgtcg actcactggc gctttgttcc ag                                          32
```

HIGH EFFICIENCY RETROVIRAL VECTOR WHICH CONTAINS GENETICALLY ENGINEERED CELLULAR NON-CODING SEQUENCE HARBORING SPLICING ACCEPTOR

CROSS REFERENCE TO RELATED APPLICATION

This application is the National Stage of International Application No. PCT/KR01/01515, filed Sep. 8, 2001.

FIELD OF THE INVENTION

The present invention relates to a highly efficient and safe retroviral vector for gene therapy, derived from murine leukemia virus (MLV), which contains a mutated heterologous splicing acceptor and lacks MLV coding sequences.

BACKGROUND OF THE INVENTION

Retroviral vectors derived from murine leukemia virus (MLV) have been employed in more than 50% of approved clinical gene therapy trials (Wiley—The Journal of Gene Medicine Website. However, one of the major limiting factors hindering a wider use of these vectors is that the level of gene expression is does not get high enough to give clear therapeutic effects. The present inventors previously constructed retroviral vectors that contains no viral coding sequence and harbors a heterologous splicing acceptor sequence from cellular or other viral genes (KR Patent Laid-Open Publication No. 2000-6334). One of the vectors contains a splicing acceptor from the human EF1α gene. This vector gives a significantly higher level of gene expression than the control vector lacking such a splicing acceptor sequence. However one problem with this vector was that viral titer varied depending on the packaging lines used. For example, when the NIH3T3-based PG13 line was used, viral titer decreased about 10 folds. In FLYA13 derived from HT1080 cells, there was a 3-fold decrease in viral titer. Results from RNA analysis indicated that low viral titer is due to highly efficient splicing of the genomic size transcript containing the packaging signal sequence.

The present invention relates to further improvement of this retroviral vector by introducing mutations into the region around the splicing acceptor. Introduction of these mutations make a retroviral vector produce viral titer close to that of the control, while still producing high levels of gene expression. Therefore, this vector should be much more effective than others in retroviral gene therapy.

SUMMARY OF THE INVENTION

The objective of the present invention is to provide a safe and highly efficient retroviral vector that is devoid of the risk of RCR production and still capable of expressing a foreign gene efficiently which can be used in gene therapy.

In accordance with the aspect of the present invention, the retroviral vector derived from the murine leukemia virus (MLV) comprises
1) a region of a non-coding sequence of the elongation factor EF1α as an heterologous gene-derived non-coding sequence inserted upstream from the multi-cloning site, and
2) a mutation introduced downstream from the splicing acceptor within the non-coding sequence of EF1α.

BRIEF DESCRIPTION OF THE DRAWINGS

The above mentioned, and other goals and features of the present invention will become apparent from the following descriptions of the invention taken in conjunction with the accompanying drawings; which respectively show.

DETAILED DESCRIPTION OF THE INVENTION

The present invention provides an MLV (murine leukemia virus)-based retroviral vector that does not have any viral-coding sequences but does include a part of a non-coding sequence of the elongation factor EF 1α inserted upstream from the multi-cloning site to supply a splicing acceptor, and a mutation introduced downstream from the splicing acceptor within the non-coding sequence of EF 1α.

In the present invention, "a non-coding sequence" describes a genomic region containing an intron and exon region which can be transcribed but not translated.

Particularly, the non-coding sequence of EF1α in the retrovirus vector of the present invention is derived from a human cell. It contains a part of an intron and exon 2 sequence, preferably a sequence just before the translation initiation codon of exon 2, more specifically the nucleotide sequence of SEQ ID NO. 1 which corresponds to the portion of the human EF1α gene from the 3' end to just before the translation initiation codon of exon 2 (if a point of transcription initiation codon of EF1α gene is taken for +1, it corresponds to the sequence from +773 to +1006).

The inventive retroviral vector also has a mutation introduced in the heterologous gene-derived non-coding sequence in order to acquire an optimum balance among gene expression, splicing, and translational efficiencies.

It is desirable that the mutation occurs downstream from the splicing acceptor, specifically just behind the splicing acceptor. It has been confirmed that the sequence surrounding the splicing acceptor, in particular, the sequence of the exon region adjacent to the splicing acceptor plays an important role in splicing. A preferable mutation, for example, is to replaced the 205$^{th}$ and 206$^{th}$ GT (guanine-thymine) base pair (corresponding to +977 and +978, respectively) in the sequence of SEQ ID NO. 1 with a CC (cytosine-cytosine) base pair.

The retroviral vector of the present invention may further be comprised of a heterologous promoter or IRES (internal ribosomal entry site) at the downstream of the multi-cloning site for the purpose of expressing two or more foreign genes.

Furthermore, U3 in MLV-based 5' LTR of the inventive retroviral vector, or a part thereof, may be replaced with a heterologous promoter, preferably the HCMV IE (human cytomegalovirus immediately-early) promoter.

The inventive retroviral vector may further comprise of a selectable marker gene, e.g., NEO (neomycin resistance) gene, and MDR (multidrug resistance) gene. The use of the human MDR gene as a selectable marker may be advantageous in that it is easy to prepare a producing cell line and prevent harmful side effects, such as CTL (cytotoxic T lymphocytes) reactions.

Figure 1:
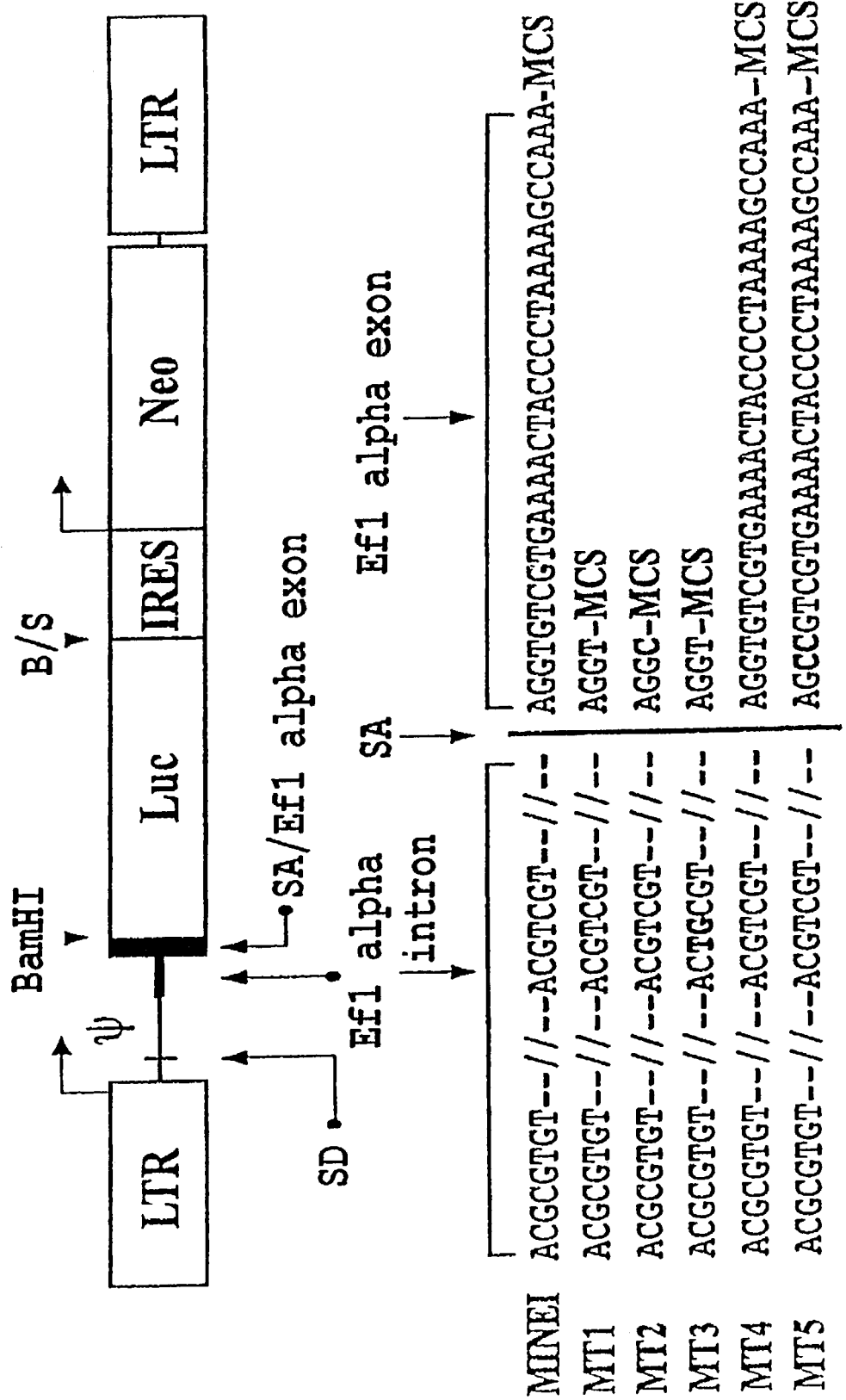
FIG. 1: the sequences of vectors MT1, 2, 3, 4 and 5, each having a mutation introduced in the non-coding sequence, that contains a region of the intron and exon 2 of the human EF1α gene inserted into vector pMIN-EI (SEO ID NOS:19 and 20)

A "wild-type" or "wild-type vector" is used as a control to make comparisons with the inventive retroviral vector that has a mutation. The wild-type vector is composed of an unmodified part of the EF1α non-coding sequence at the upstream of the multi-cloning site in order to increase the gene expression level by providing splicing capability. Used in the present invention as a control is the wild-type MT4 which has the following sequence showing in FIG. 1.

An ideal example of the retroviral vector provided by the present invention contains
1) nucleotide sequences derived from the original MLV vector that corresponds to the 5' LTR, the minimal packaging sequence containing the splicing acceptor at the upstream of the original gag gene, a poly-purine track, and a 3' LTR;
2) a multi-cloning site;
3) a region of the nucleotide sequence of EF1α, starting from the 3' end of the intron to just before the translation initiation codon of exon 2, inserted between the minimal packaging sequence and the multi-cloning site; and
4) an SV40 minimal promoter or an internal ribosomal entry site (IRES) downstream of the multi-cloning site only when a second gene expression is required.

More preferably, the present invention provides a retroviral vector MT5 comprising
1) nucleotide sequences derived from the original MLV vector which are 5' LTR, the minimal packaging sequence containing the splicing donor at the upstream of the original gag gene, poly-purine track, and 3' LTR;
2) a multi-cloning site;
3) a part of the nucleotide sequence of EF1α, which starts from the 3' end of the intron to just before the translation initiation codon of exon 2, inserted between the minimal packaging sequence and the multi-cloning site;
4) an internal ribosomal entry site (IRES) downstream from the multi-cloning site; and
5) a GC base pair replacing the GT base pair at the +977~+978 site, downstream of the splicing acceptor.

Hereinafter, the present invention is described in detail.

1. Construction of MLV-Based Retroviral Vector MIN-EI Having No Viral Coding Sequences and Containing the Non-Coding Sequence of Human EF1α

Procedures for preparing the MLV-based retroviral vector MIN that is devoid of its MLV-coding gag, env and pol gene sequences, and MIN-EI that contains the non-coding sequence of the human EF1α at the upstream of the multi-cloning site of vector MIN are described in the KR Patent Laid-Open Publication No. 2000-6334 in detail.

The structural characteristics of the vectors MIN and MIN-EI are as follows:

Vector MIN contains 1) the non-coding sequence just before the gag coding region, containing the 5' LTR and the splicing acceptor of the MLV genome; 2) a multi-cloning site; 3) IRES-neo cassette; and 4) a 3' non-translation region, poly-purine track and 3' LTR, in that order.

Vector MIN-EI has the sequence of SEQ ID NO. 1, which corresponds to the sequence of the EF1α intron and exon 2 just before the translation initiation codon, inserted upstream of the multi-cloning site of vector MIN.

2. Efficiencies of Retroviral Vectors Having a Non-Coding Sequence of EF1α in Various Packaging Cells To generate the optimized retroviral vector, delicate balance between transcription, and splicing efficiency is required for the efficient expression of a therapeutic gene in target cells. The level of gene expression of retroviral vector MIN-EI is 3~5 fold higher than that of vector MIN (KR Patent Laid-Open Publication No. 2000-6334) in such a packaging cell lines as Phoenix, 293T, FlyA13, and PG13. However, vector MIN-EI exhibits a reduced viral titer in FlyA 13 or PG 13 cell lines, probably due to the highly efficient splicing and generally low transcriptional activity of FlyA13 or PG13 cell lines. Accordingly, there exhibits a need to develop a retroviral vector having both a high level of gene expression and an improved viral titer.

3. Construction of Retroviral Vectors Containing Modified Non-Coding Sequences of EF1α gene In order to fulfill the above-mentioned need, modified retroviral vectors are constructed by way of introducing a mutation around the intron and the splicing acceptor of the EF1α gene of MIN-EI.

5 mutant vectors that were constructed in the present invention are:
1) MT1, wherein no mutation is introduced at the splicing acceptor and the region corresponding to exon 2 of EF1α is deleted;
2) MT2, wherein a mutation is introduced downstream from the splicing acceptor and the region corresponding to exon 2 of EF1α is deleted;
3) MT3, wherein a mutation is introduced upstream from the splicing acceptor and the region corresponding to exon 2 of EF1α is removed;
4) MT4 is a wild-type having no mutation at the splicing acceptor; and
5) MT5, wherein a mutation is introduced downstream from the splicing acceptor In the cases of using the luciferase gene as a reporter gene, modified vectors MT1, 2, and 3 show a reduced viral titer than wild-type MT4, but vector MT5 gives 2~3 folds higher viral titer than wild-type MT4. The splicing efficiency of vector MT5 is somewhat low, about 70~80% less than that of wild-type MT4, however the total amount of the gene expressed increases due to the enhanced viral titer. Such an enhancement in the total transduction efficiency is also observed with vector MT5 carrying a human interleukin-1 receptor antagonist (IL-1ra) gene instead of the luciferase gene as a reporter gene.

Thus, vector MT5 is identified as a novel, safe vector that provides high level of gene expression as well as high viral titer. E. coli strain JM109 transformed with vector MT5 has been designated as MT5(JM) and deposited at the Korean Culture Center of Microorganisms (KCCM) on Jul. 28, 2000 (Accession Number: KCCM-10205).

4. Construction of Vector MTM5 Containing the Modified EF1α Non-Coding Sequence and MDR Selectable Marker Gene Vectors carrying the human MDR gene as a selectable marker gene have also been constructed and designated as MTM5, which give an excellent transduction efficiency due to their enhanced viral titer.

The present invention is described in detail in the examples below. It should be evident that the following examples are intended to further illustrate the present invention without limiting its scope.

EXAMPLES

Example 1

Efficiency of Vector MIN-EI in Various Packaging Cell Lines

In order to investigate the efficiency of vector MIN-EI, containing the intron and non-coding sequence of the EF1α gene in various packaging cell lines, the gene expression level and viral titer was examined using commonly used packaging cell lines such as Phoenix (ATCC SD3443, Md., USA), FlyA13 (Cosset et al., *J. Virol.* 69: 7430–7436, 1995), and PG13 (ATCC CRL10686, Md., USA) cell lines.

MIN-CAT and MFG-CAT (Byun et al., *Gene Ther.* 3: 780–788, 1996) were employed as controls. MIN-EI-CAT and MIN-CAT were constructed by inserting the BamHI fragment of the plasmid pCRII-CAT (KR Patent Application No. 1998-24478), containing CAT (chloramphenicol acetyltransferase) gene, into the BamHI sites of vectors MIN-EI and MIN, respectively. Vector MFG-CAT was constructed by inserting the NcoI-BamHI fragment of pCRII-CAT into the NcoI-BamHI site of vector MFG (Byun et al., *Gene Ther.* 3: 780–788, 1996).

Phoenix and FlyA13 cells were each transfected with vector MIN-EI-CAT, MIN-CAT or MFG-CAT, cultured for 48 hours, and the protein extract from the cells was used to measure the level of gene expression. Cell-free virus was prepared by filtering the cell culture supernatant through a 0.45 μm filter paper. After 2 sets of NIH3T3 cells were transduced with the cell-free viral supernatant and incubated for 48 hours, 1 set of NIH3T3 cells was employed for measuring the CAT activity. The other set of NIH3T3 cells was used for determining viral titer and transduction efficiency by counting the number of G418 resistance colonies (see table 1 and 2).

In the case of PG13 cells, producer lines were generated to obtain the virus. Because it is impossible to get high viral titer using transient transfection method in PG 13 cells. Namely, about 0.1 m.o.i of the cell-free virus obtained by using Phoenix cells were allowed to infect PG13 cells, and the G418 resistant cell line was selected after treatment with G418 for 2 weeks. The cell free viral supernatant was used to transduce 2 sets of HT1080 cells. They were incubated for 48 hours, and subjected to CAT assay and viral titer measurements, respectively (see table 3).

The CAT activity was measured by the following procedure: The transduced cells were harvested, washed once with 1 ml of PBS (phosphate-buffered saline), and then resuspended in 0.25 M of Tris buffer (pH 7.5). The cells were lysed by way of conducting 3 freezing (in dry-ice)-thawing (in 37° C. water bath) cycles. After heating at 60° C. for 7 minutes to inactivate the deacetylase, the resulting cell extract was subjected to centrifuge spinning at 12,000 rpm for 10 minutes, and the supernatant was collected. The protein concentration was quantified by Bradford's method. A fixed amount of protein was mixed with 1 μl of $^{14}$C-chloramphenicol (60 mCi/mmol, 0.1 mCi/ml), 2 μl of acetyl-coenzyme A (40 mM), and an appropriate amount of 0.25 M Tris buffer (pH 7.5) and then incubated at 37° C. After the reaction, chloramphenicol was extracted with ethyl acetate, and concentrated under a reduced pressure. The residue was resuspended in 15 μl of ethyl acetate, loaded onto a thin layer chromatography (TLC) plate, and developed using a solvent (95% chloroform, 5% methanol). The TLC plate was dried and then exposed to an X-ray film or brought to a phosphoimage analyzer, so that the acetylation level of the chloramphenicol could be measured. The CAT activity was measured by calculating the radioactivity ratio of the acetylated chloramphenicol to the total chloramphenicol.

TABLE 1

Comparison of retroviral vector efficiency in Phoenix cell

| | Relative CAT activity* | | | |
|---|---|---|---|---|
| | Transient- | Transduction | | |
| Vector | transduction | Transient | Stable | Viral titer |
| MIN | 1.0 | 1.0 | 1.0 | 1.0 |
| MIN-EI | 3.5 ± 0.4 | 3.3 ± 0.4 | 3.0 ± 0.6 | 1.1 ± 0.2 |
| MFG | 1.0 ± 0.2 | 1.1 ± 0.3 | 0.4 ± 0.2 | 1.0 ± 0.3 |

*Based on the CAT activity of vector MIN (radioactivity of acetylated chloramphenicol/radioactivity of total chloramphenicol).

As can be seen in Table 1, when using Phoenix cells as a packaging cell line, the CAT activity of MIN-EI was 3~4 folds higher than that of MIN or MFG. This suggests that the gene expression efficiency of MIN-EI is superior to that of the others. There were no significant changes in viral titer among these vectors, and thus, the measured CAT activity of the transduced NIH3T3 cell directly reflects the gene expression efficiency.

TABLE 2

Comparison of retroviral vector efficiency in FlyA13 cells

| | Relative CAT activity | | | |
|---|---|---|---|---|
| | Transient- | Transduction | | |
| Vector | transduction | Transient | Stable | Viral titer |
| MIN | 1.0 | 1.0 | 1.0 | 1.0 |
| MIN-EI | 4.5 ± 0.7 | 0.6 ± 0.1 | 2.2 ± 0.5 | 0.3 ± 0.1 |
| MFG | 1.7 ± 0.3 | 0.8 ± 0.2 | 0.5 ± 0.1 | 1.1 ± 0.2 |

TABLE 3

Comparison of retroviral vector efficiency in PG13 cell

| | Transduction | | |
|---|---|---|---|
| Vector | Transient | Stable | Viral titer |
| MIN | 1.0 | 1.0 | 1.0 |
| MIN-EI | 0.8 | 7.0 | 0.1 |
| MFG | 2.6 | 2.9 | 1.0 |

However, when using FlyA13 (see Table 2) or PG13 (see Table 3) as a packaging cell line, the viral titer of MIN-EI was quite low, only one third to one tenth of that for MIN or MFG.

Example 2

Viral Productivity of MIN-EI

To examine the reason why viral titer varies in accordance with the packaging cell line used, northern blotting analyses were performed. First, cytoplasmic RNAs were extracted from Phoenix cells transfected with MFG and MIN-EI, respectively, and also from PG13 cells producing MFG and MIN-EI, respectively, using the Guanidine thiocyanate-cesium method as follows: Cells cultured in a 100 mm dish were washed twice with PBS and 3 ml of guanidine buffer solution was added thereafter. Upon becoming transparent, the mixture was homogenized using a syringe, poured into a polyaloma tube (Beckman) containing 2 μl of 5.7 M $CsCl_2$, and centrifuged at 20° C., 29,000 rpm for 16 hours to obtain an RNA pellet. The RNA pellet was dissolved in 150 μl of distilled water containing DEPC, and subjected to ethanol precipitation to obtain 50 μl of RNA solution.

20 μg of RNA was mixed with 20 μl of formamide, 10 μl of 37% formaldehyde, and 10 μl of 10× MOPS. The mixture was heated at 70° C. for 10 minutes, and subjected to electrophoresis on a formaldehyde-agarose gel at 50 mA. The gel was successively soaked in 50 mM NaOH, 10 mM NaCl for 10 min and 20× SSC solution (3 M NaCl, 0.3 M sodium citrate) for 45 minutes. The treated RNA was separated, transferred onto a nitrocellulose membrane using capillary means, and fixed at 80° C. for 1 hour. After prehybridization with the ExpressHyb hybridization solution (Clontech, USA) at 65° C. for 30 minutes, the nitrocellulose membrane was subjected to a hybridization reaction using isotope-labeled CAT DNA fragment. The nitrocellulose membrane was washed twice with a buffer, and exposed to an X-ray film, and the resulting bands for genomic RNA and subgenomic RNA were each quantified with a phosphoimage analyzer.

TABLE 4

Comparison of RNA composition according to packaging cell lines

| | Phoenix cell line | | | | PG13 cell line | | |
|---|---|---|---|---|---|---|---|
| | The amount of RNA | | | | The amount of RNA | | |
| Vector | Gemo. RNA | Sub-geno. RNA | Total RNA | Vector | Gemo. RNA | Sub-geno. RNA | Total RNA |
| MFG | 257 (69%)* | 118 (31%) | 375 (100%) | MFG | 241 (63%) | 139 (37%) | 380 (100%) |
| MIN-EI | 187 (6%) | 2834 (94%) | 3021 (100%) | MIN-EI | 22 (5%) | 388 (95%) | 410 (100%) |

*( ) represents the ratio of respective genomic RNA and subgenomic RNA to total RNA As the results in Table 4 shows, the splicing efficiency of MIN-EI does not vary significantly with the packaging cell lines. In the Phoenix cell line, MIN-EI synthesized a considerably larger amount of subgenomic RNA than MFG, and exhibited a generally high transcriptional level. This result explains why MIN-EI shows a high level of gene expression. However, in the PG13 cell line, the transcriptional activity of MIN-EI was significantly reduced, while the splicing efficiency was maintained at about the same level as in the Phoenix cell line. Thus, the absolute amount of genomic RNA became low, which resulted in a reduction in viral titer.

Namely, in the Phoenix cell line, efficient splicing occurs by the action of the intron and non-coding sequence of the EF1α gene, giving more subgenomic RNA than genomic RNA, resulting in increased level of gene expression. Moreover, as genomic RNA synthesis is facilitated by a high transcriptional activity, the viral titer also remains high. However, in FlyA13 and PG13 cell lines, splicing progresses efficiently, giving a large relative amount of subgenomic RNA, but the total amount of genomic RNA is reduced significantly resulting in low viral titer.

Example 3

Construction of Retroviral Vector Having Both a Mutation at the EF1α Intron and a Non-Coding Sequence In order to develop an improved vector drive a high level of gene expression without compromising viral titer, the mutation was introduced to maintain delicate balance between splicing efficiency and viral titer. 5 mutant vectors were constructed by introducing a mutation into and around the intron and splicing acceptor of the EF1α gene of MIN-EI (see FIG. 1):

1) MT1 wherein no mutation is introduced at the splicing acceptor and the region corresponding to exon 2 of EF1α is deleted;

2) MT2 wherein a mutation is introduced downstream from the splicing acceptor and the region corresponding to exon 2 of EF1α is deleted;

3) MT3 wherein a mutation is introduced upstream from the splicing acceptor and the region corresponding to exon 2 of EF1α is removed;

4) MT4 is a wild-type having no mutation introduced at the splicing acceptor; and 5) MT5 wherein a mutation is introduced at the downstream from the splicing acceptor (3-1) Construction of MT1

To construct MT1, PCR was conducted using plasmid pMIN-EI (KR Patent Application No. 1999-23398) as a PCR template and the synthetic oligonucleotides of SEQ ID NO. 2 (EI5') and 3 (EI3'-1s) as a primer pair.

100 μl of the PCR reaction solution containing 200 ng of the template plasmid DNA and 1 μl each of the primers (10 pmol/μl ) was subjected to 30 cycles of PCR amplification reaction, each cycle being conducted for 1 minute at 94° C. (denaturation), 1 minute at 50° C. (annealing) and 1 minute 30 seconcds at 72° C. (polymerization).

Figure 2:
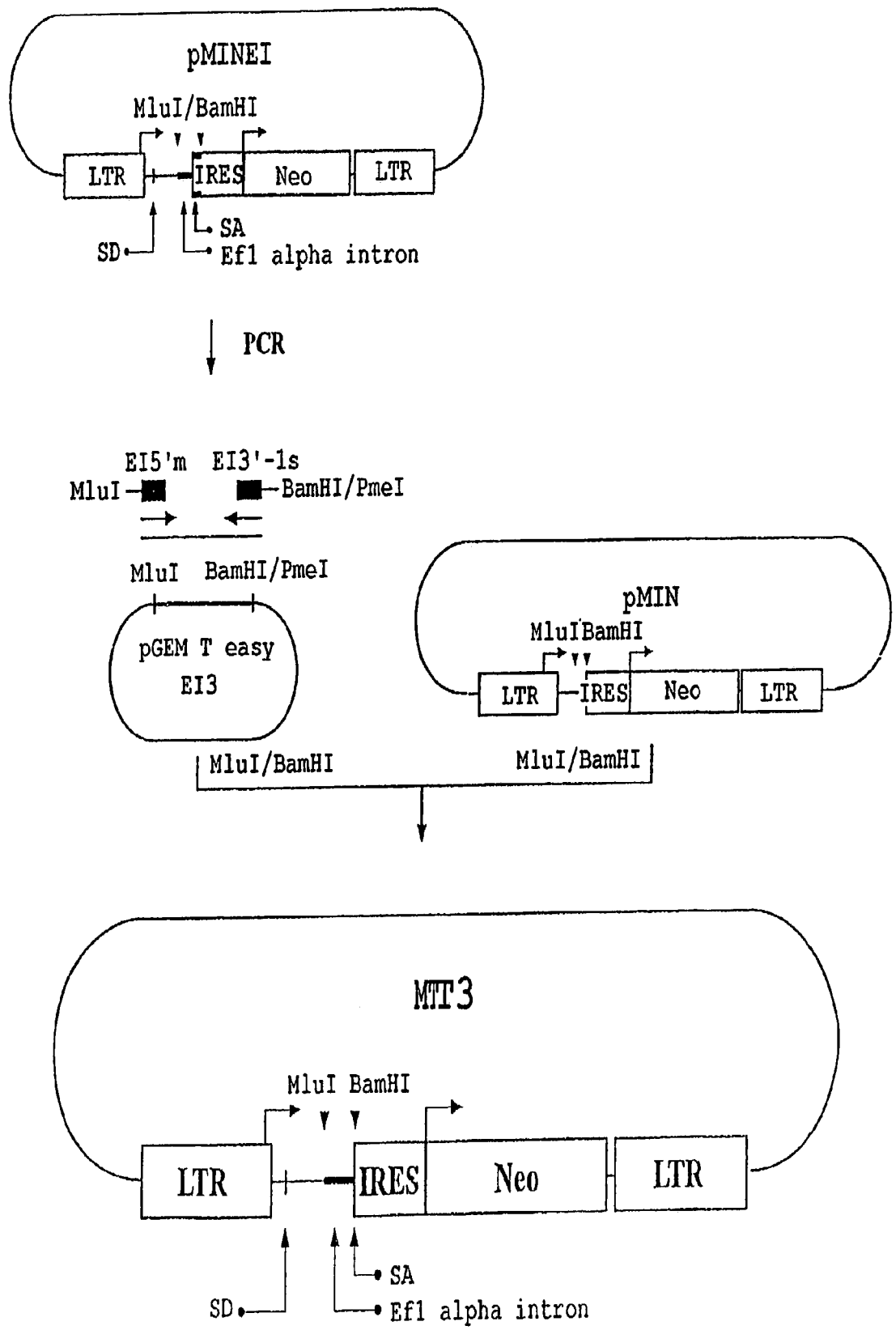
FIG. 2: the procedure for preparing MT1.

After the amplified fragment of the EF1α intron was cloned into the pGEM T easy vector (Promega, Wis., USA), the MulI-BamHI fragment comprising MCS (SEQ ID NO:16) was excised and inserted into the MulI-BamHI site of pMIN to generate MTI (see FIG. 2).

(3-2) Construction of MT2

MT2 was constructed by PCR as in the Example (3-1) using the plasmid pMIN-EI as a PCR template and the synthetic oligonucleotides of SEQ ID NO. 2 (EI5') and 4 (EI3'-2s) as a primer pair.

Figure 3:
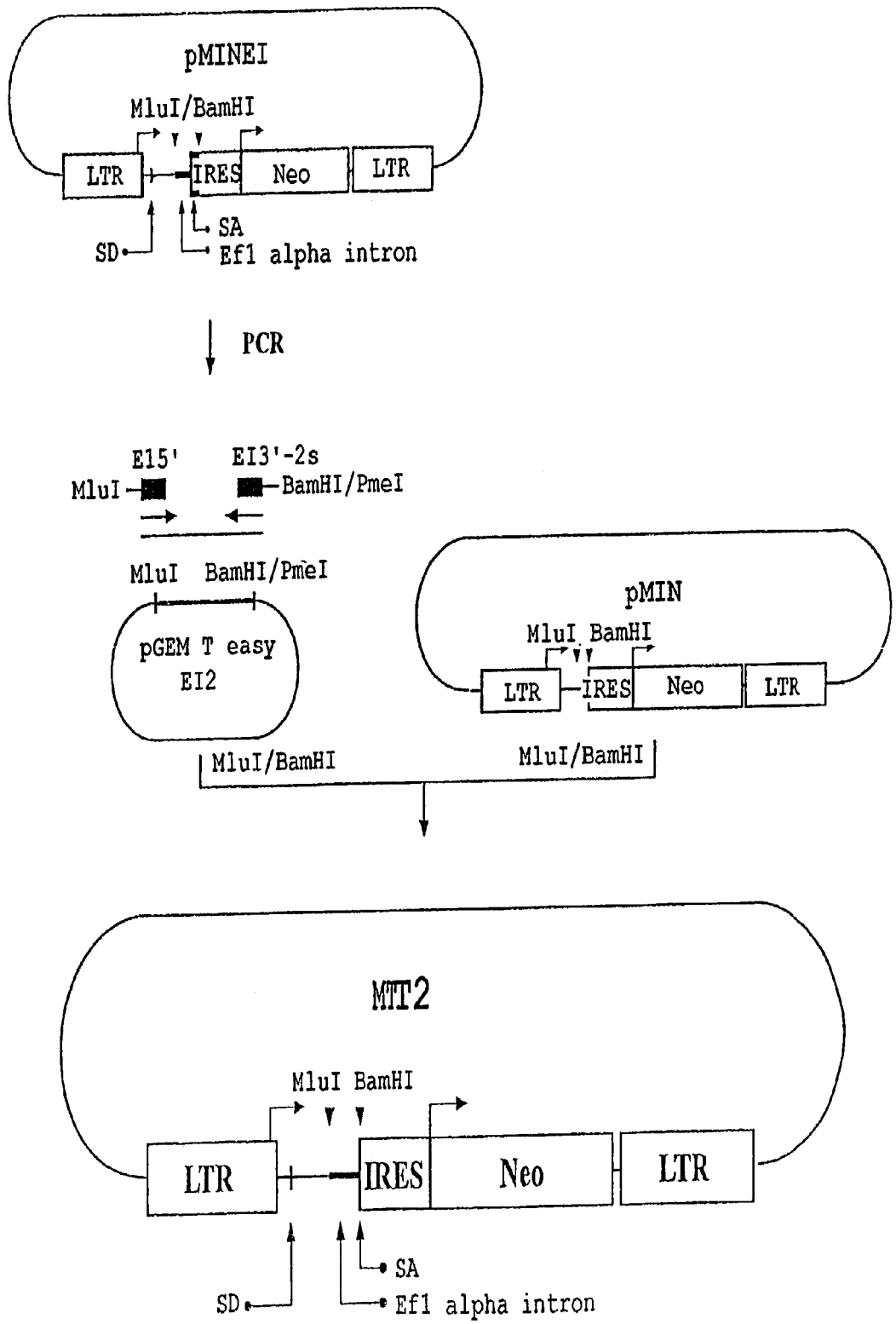
FIG. 3: the procedure for preparing MT2.

The PCR amplified fragment of the EF1α intron having a mutation introduced downstream from the splicing acceptor was cloned into the pGEM T easy vector (Promega, Wis., USA), and the MulI-BamHI fragment comprising MCS (SEQ ID NO:16) was excised and inserted into the MulI-BamHI site of pMIN to generate MT2 (see FIG. 3).

(3-3) Construction of MT3

MT3 was constructed by PCR as in the Example (3-1) using the plasmid pMIN-EI as a PCR template and the synthetic oligonucleotides of SEQ ID NO. 5 (EI5'm) and 3 (EI3'-1s) as a primer pair.

Figure 4:
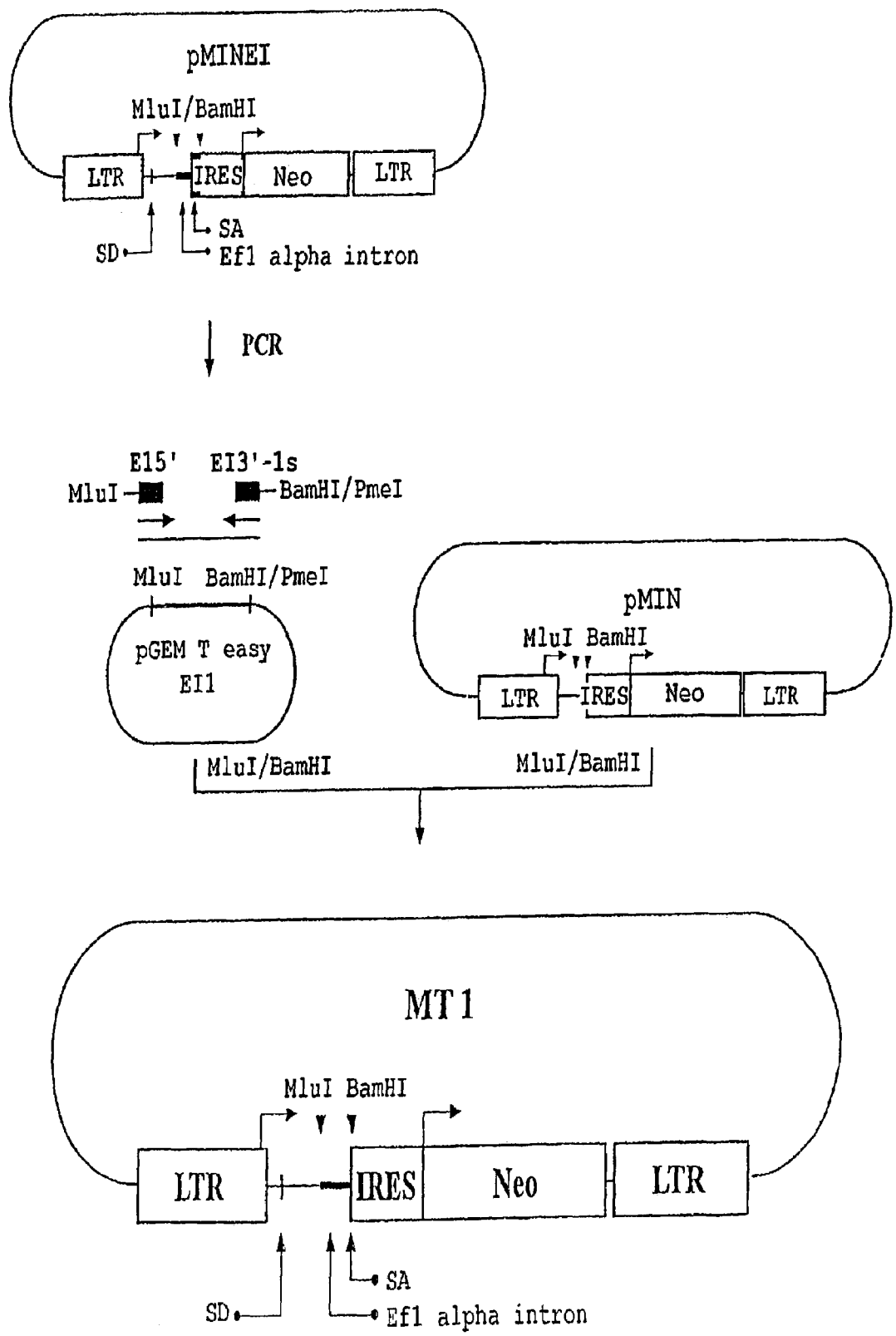
FIG. 4: the procedure for preparing MT3.

The PCR amplified fragment of the EF1α intron having a mutation introduced upstream from the splicing acceptor was cloned into the pGEM T easy vector (Promega, Wis., USA), and the MulI-BamHI fragment comprising MCS (SEQ ID NO:16) was excised and inserted into the MuII-BamHI site of pMN to generate MT3 (see FIG. 4).

(3-4) Construction of MT4

The wild-type vector MT4 was constructed by PCR as in the Example (3-1) using the plasmid pMIN-EI as a PCR template and the synthetic oligonucleotides of SEQ ID NO. 2 (EI5') and 6 (EI3'-11) as a primer pair.

Figure 5:
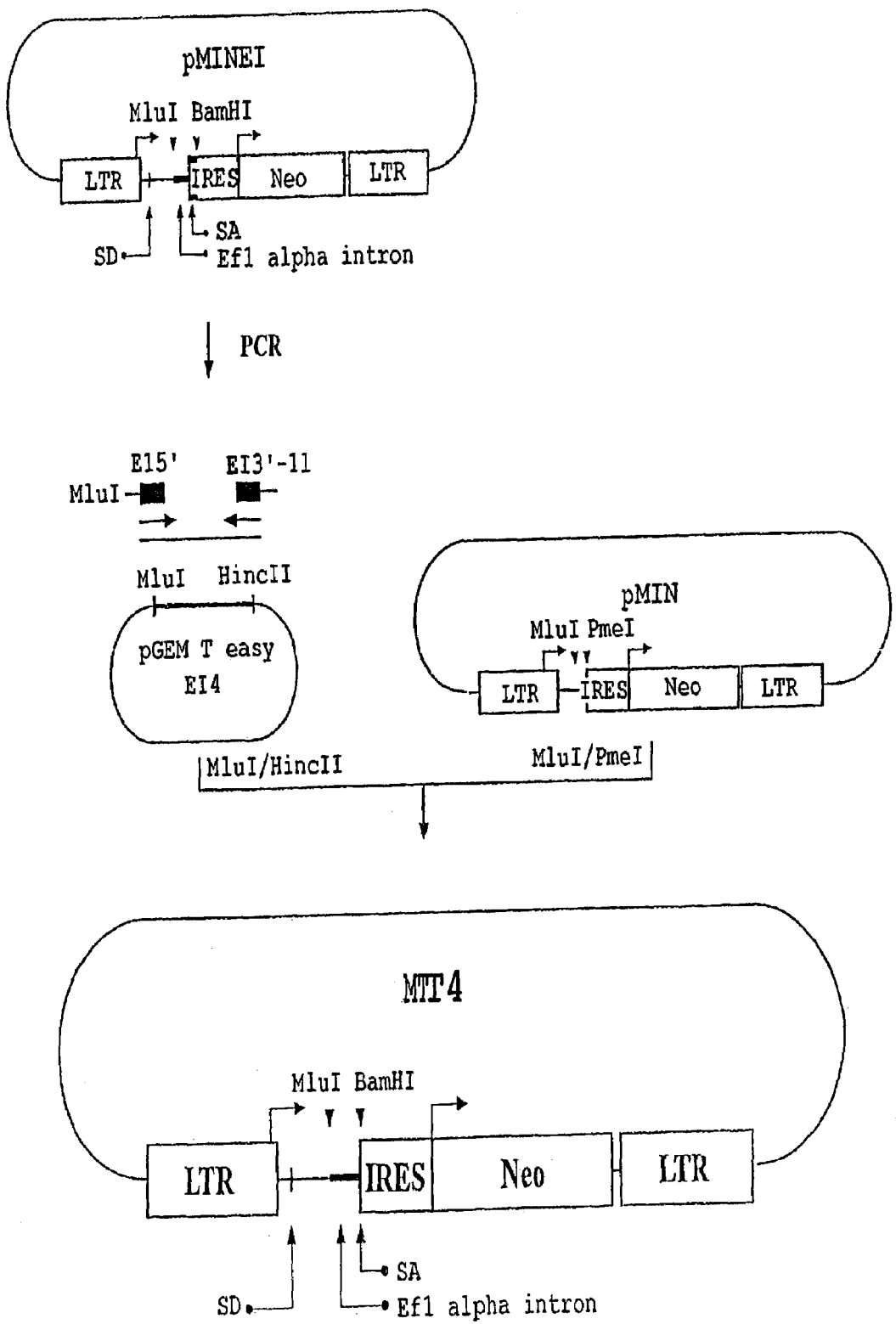
FIG. 5: the procedure for preparing wild-type MT4.
Figure 6:
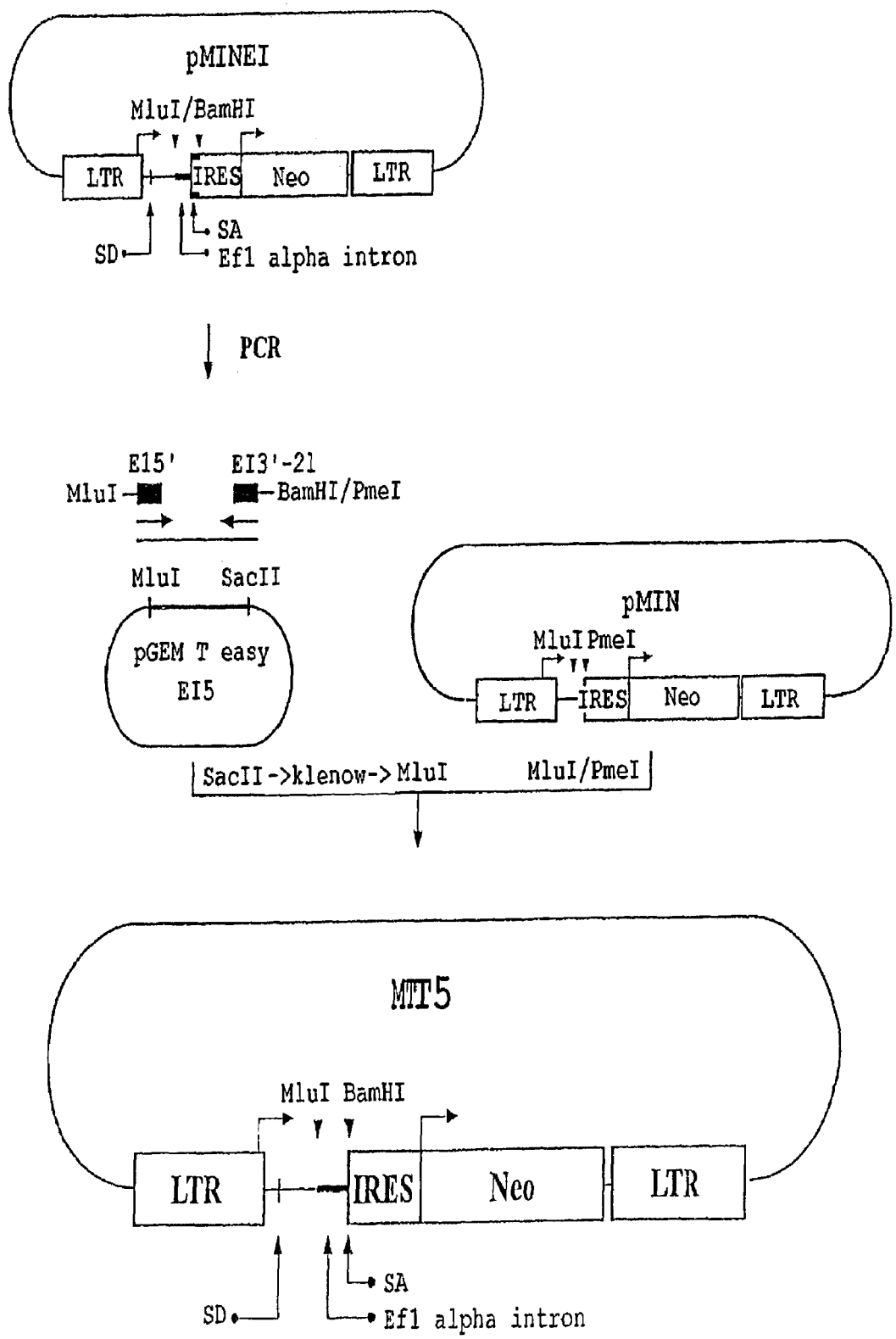
FIG. 6: the procedure for preparing MT5.

The PCR amplifed fragment of the EFIα intron was cloned into vector pGEM T easy (Promega, Wis., USA), and the MluI-HincII fragment comprising MCS2 (SEQ ID NO:17) was excised and inserted in the MluI-PmeI site of pMIN-EI to generate MT4 (see FIG. 5).

(3-5) Construction of MT5

MT5 was constructed by PCR as in the Example (2-1) using the plasmid pMIN-EI as a PCR template and the synthetic oligonucleotides of SEQ ID NO. 2 (EI5') and 7 (EI3'-2l) as a primer pair.

The PCR amplifed fragment of the EFIα intron was cloned into vector pGEM T easy (Promega, Wis., USA), and the MluI-SacII fragment comprising MCS2 (SEQ ID NO:18) was excised and inserted in the MluI-PmeI site of pMIN-EI to generate MT4 (see FIG. 5).

Example 4

Figure 7:
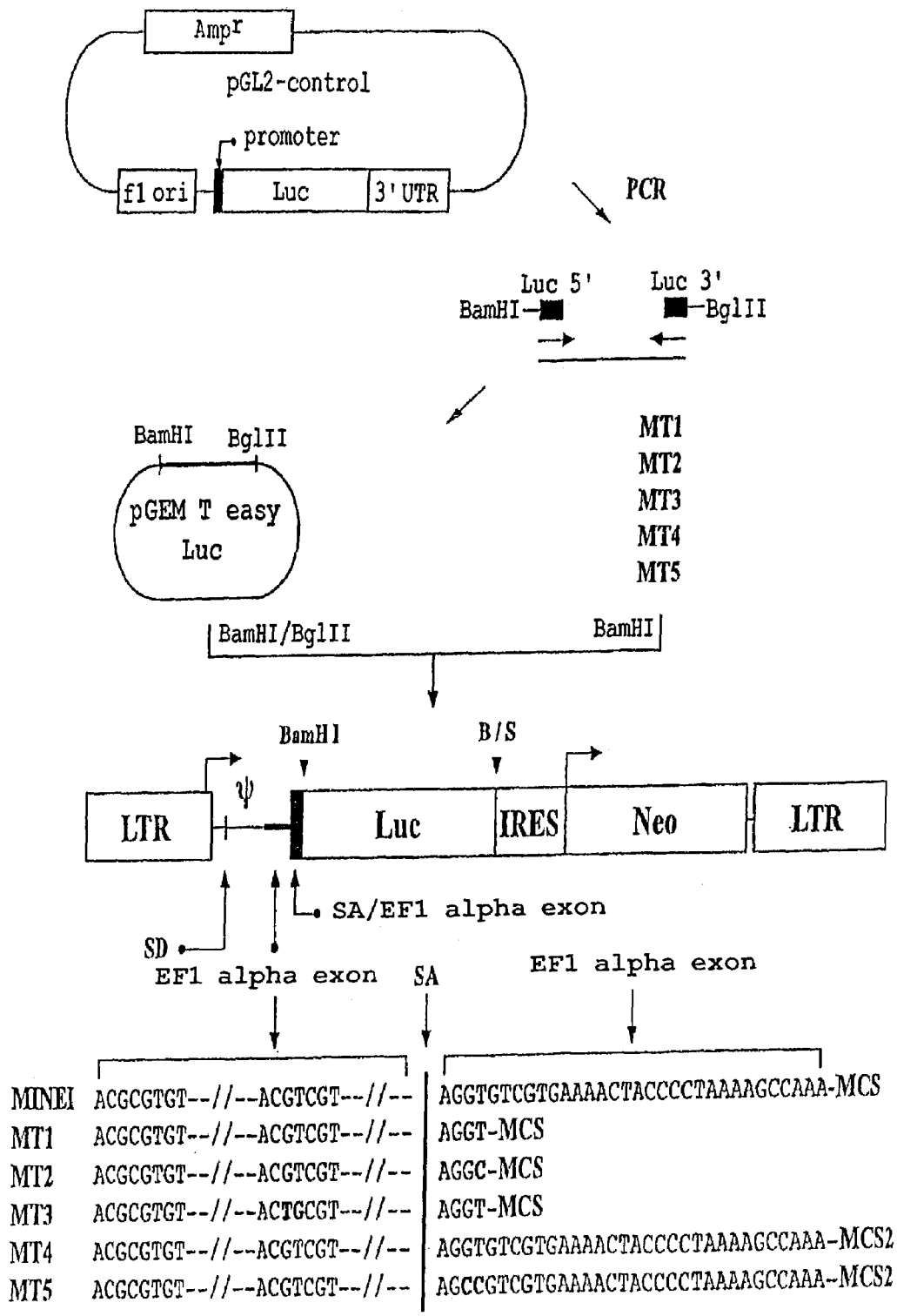
FIG. 7: the procedure for preparing a vector which contains a luciferase (Luc) gene (SEG ID NOS:19 and 20)
Figure 8:
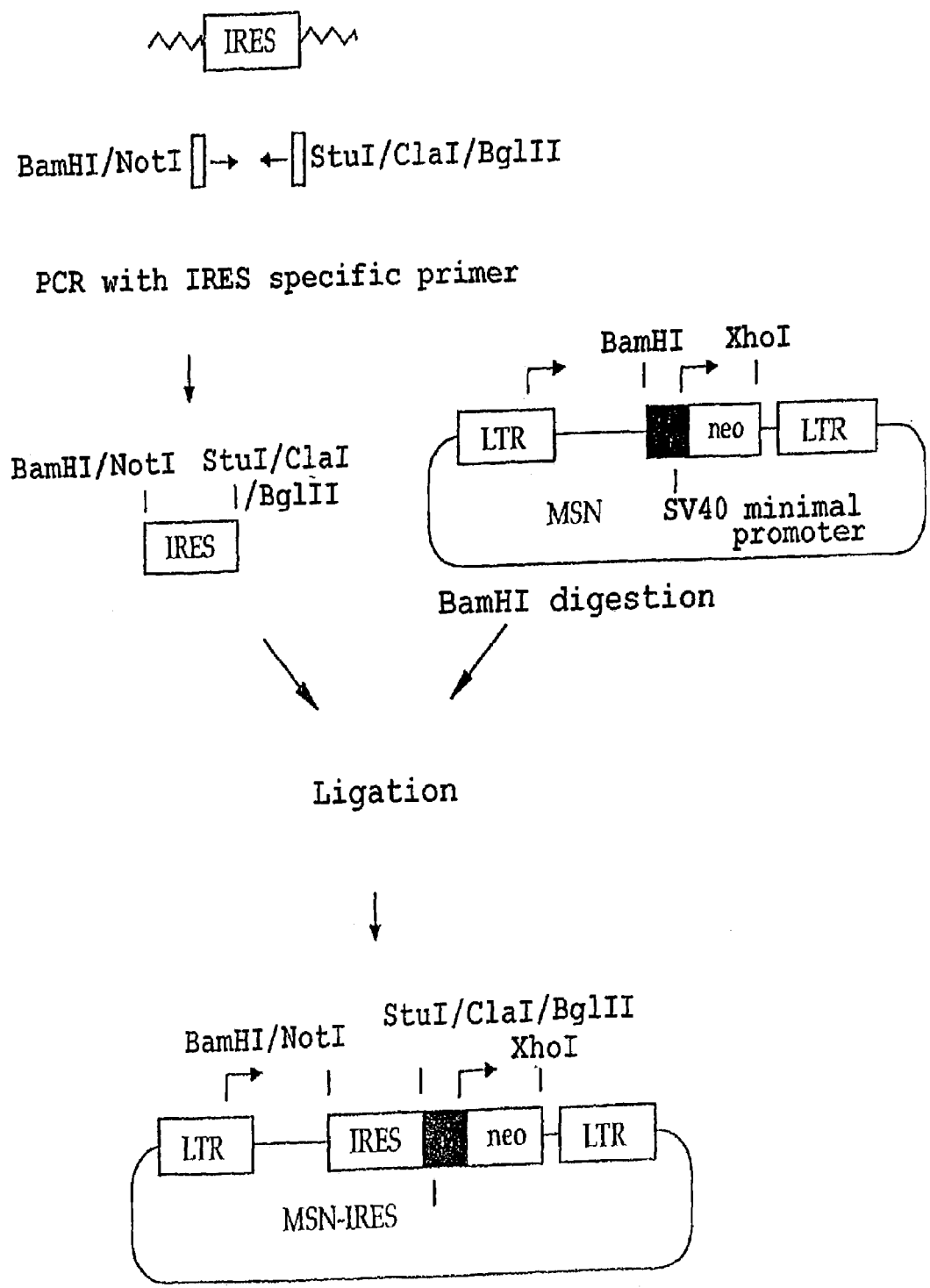
FIG. 8: the procedure for IRES gene cloning.

Efficiencies of Inventive Vectors Carrying Luc Gene (4-1) Cloning of Luciferase (Luc) Gene The Luc gene was amplified by PCR using the pGL2 control vector (Promega, Wis., USA) as a template and the synthetic oligonucleotides of in SEQ ID NOs. 8 (Luc 5') and 9 (Luc 3') as a primer pair. The amplified fragment was inserted into the pGEM T easy vector (Promega, Wis., USA) in order to generate the pGEM T easy-Luc vector (see FIG. 7). The fragment containing the luciferase gene obtained by treating the pGEM T easy-Luc vector with BamHI/BglII was inserted into the BamHI site of each vector prepared in Example 2, to generate the luciferase expression vectors shown in FIG. 7.

(4-2) Measurement of Luciferase Activity

MT1, 2, 3, 4, and 5 containing the luciferase gene were each transfected into Phoenix cells, and the cells were incubated for 48 hours. Cell-free viral supernatants were used to transduce NIH3T3 cells. Luciferase activities of from transfected and transduced cells, respectively, were measured. The luciferase activity and viral titer of the G418 resistant stable cell line (see Table 5) were also measured. In Table 5, the luciferase activity of each retroviral vector is represented as a relative value based on that of the wild-type MT4 vector.

The luciferase activity was measured as follows: The harvested cells were washed with 1 ml of PBS. After removing PBS completely, the cells were resuspended in an appropriate amount of 1× reporter lysis buffer (Promega, Wis., USA) and reacted at room temperature for 5 minutes. The reaction mixture was subjected to centrifuge spinning at 12,000 rpm for 1 minute, and the supernatant was collected. The protein concentration in the extract was quantified by Bradford's method. A fixed amount of protein was mixed with 100 μl of the luciferase assay reagent (Promega, Wis., USA), and the reaction mixture was transferred to a 96 well plate in order to measure the Luc activity with a luminometer (see FIG. 5).

TABLE 5

Comparison of mutant vector efficiency

| | Relative luciferase activity | | | |
|---|---|---|---|---|
| | Transient | Transduction | | |
| Vector | transduction | Transient | Stable | Viral titer |
| MT1 | 0.4 | 0.2 | — | 0.1 |
| MT2 | 0.8 | 1.0 | — | 0.6 |
| MT3 | 0.1 | 0.2 | — | 0.1 |
| MT4 | 1.0 | 1.0 | 1.0 | 1.0 |
| MT5 | 0.5 | 1.3 | 0.9 | 1.6 |

As can be seen in Table 5, both the gene expression level and the viral titer of MT1, 2 and 3 were lower than that of control MT4 containing wild-type EF1α intron and a splicing acceptor sequence. The gene expression level of MT5 in the Phoenix cell reached a 50~70% level of that of MT4, but its viral titer increased about 2 folds, and the luciferase activity in transduced NIH3T3 cells also increased. That is, the splicing efficiency of MT5 was slightly lower than that of MT4, giving a reduced amount of subgenomic RNA. Therefore, the gene expression of MT5 is somewhat low but its whole transduction efficiency is enhanced due to its relatively high viral titer. The results shows that the mutation introduced downstream from the splicing acceptor is capable of maintaining the balance between splicing efficiency and the amount of genomic packageable transcript.

Example 5

Efficiencies of Inventive Vectors Carrying IL-1ra Gene and Analysis of the RNA Composition (5-1) Comparison of Efficiencies of Vectors Using IL-Ira Gene In order to examine whether the improved activity of the MT5 vector observed in Example 4 is a general phenomenon applicable to other foreign genes, the procedures of Example 4 were repeated employing the human IL-1ra gene in place of the Luc gene (see Table 6).

IL-1ra gene was obtained from peripheral blood lymphocytes. First, peripheral blood lymphocytes were obtained from the blood of normal people by using Ficoll-hypaque, and RNA was extracted and subjected to reverse transcriptase PCR (RT-PCR) in order to obtain cDNA. The IL-1ra gene fragment was amplified, using the cDNA as a template and the synthetic oligonucleotides of SEQ ID NOs. 10 (IRAP 5') and 11 (IRAP 3') as a primer pair. The amplified PCR product was inserted into the pGEM T easy vector (Promega, Wis., USA) in order to generate vector pGEM T easy-IL-1ra. A fragment containing the IL-1ra gene was obtained by treating the resulting vector with BamHI/BglII and inserted into the BamHI sites of MT4 and MT5 vectors prepared in Example 3, respectively. The resulting IL-1ra expression vectors were examined together with the vector MFG-IL-1ra (Yu et al., *Gene Ther.* 7:797–804, 2000).

Vectors MT4, MT5, and MFG containing the IL-1ra gene were each transfected into Phoenix cells, and incubated for 48 hours. The cell-free viral supernatants were used to transduce NIH3T3 cells. The amounts of IL-1ra secreted into supernatants of transfected and transduced cells were measured using human IL-1ra ELISA (R&D system, USA), and the viral titer was determined by counting the number of G418 resistant cells (see Table 6).

TABLE 6

Comparison of vector efficiency using IL-1ra gene

| Vector | Relative IL-1ra activity | | Viral titer |
|---|---|---|---|
| | Transfection | Transduction | |
| MT4 | 1.0 | 1.0 | 1.0 |
| MT5 | 0.5 | 1.5 | 1.8 |
| MFG | 0.2 | 0.3 | 1.3 |

The resultss in Table 6 demonstrates that the transduction efficiency and the viral productivity of MT5 are also enhanced when it carries the IL-1ra as a reporter gene.

(5-2) Cytoplasmic RNA

To examine whether the results obtained in the Example (5-1) are due to a change in the splicing efficiency, cytoplasmic RNA was analyzed by northern blotting. Briefly, cytoplasmic RNA was extracted from the transfected Phoenix cells and subjected to hybridization using IL-1ra gene as a probe to assess the amounts of genomic RNA and subgenomic RNA. The intensities of hybridized RNA bands were quantified with a phosphoimage analyzer (see Table 7).

TABLE 7

Composition of the Phoenix cell RNA

| Vector | The amount of RNA | | |
|---|---|---|---|
| | Genomic RNA | Subgenomic RNA | Total RNA |
| MT4 | 266 (4.5%) | 5635 (95.5%) | 5901 (100%) |
| MT5 | 408 (10.3%) | 3560 (89.7%) | 3968 (100%) |
| MFG | 257 (69%) | 118 (31)% | 375 (100%) |

The results show that subgenomic RNA of MT4 accounts for 95% of the total RNA, and the relative proportion of MT5 subgenomic RNA is about 94% as compared to MT4. On the other hand, the amount of genomic RNA observed for MT5, which is much lower than that of subgenomic RNA, is more than 2 folds higher than that observed for MT4. These results explain why MT5 gives a high viral titer in comparison with MT4.

(5-3) Efficiencies of Inventive Vectors in PG13 Cell

The retroviral vector's efficiency in the PG13 cell line which can be used in an actual clinical trial was examined. Cell-free culture solutions obtained from Phoenix cells as well as the MFG (control) virus were each transfected into PG13 cells, and G418 resistant viral producing cells were obtained. The viral supernatant of the PG13 producing cell line was transduced into HT1080 cells, and the IL-1ra activity and the viral tier of the transduced cells were measured (see Table 8)

TABLE 8

Comparison of vector efficiency in PG13 cells

| Vector | Relative IL-1ra activity | Viral titer |
|---|---|---|
| MT4 | 1.0 | 1.0 |
| MT5 | 7.0 | 3.3 |
| MFG | 5.1 | 4.0 |

As the results in Table 8 demonstrate, the viral titer of MT5 is about 3~4 folds higher than that of MT4 when PG 13 cells were used.

Example 6

Construction of Vector Containing MDR

A vector which has the same modified EF1α intron and non-coding sequence as MT5 but contains human MDR gene as a selectable marker, was constructed and designated vector MTM5.

(6-1) Cloning of IRES Gene

To generate a gene fragment of IRES (internal ribosomal entry site), PCR was performed using: the plasmid pCBIN (KR Patent Application No. 1997-48095) containing IRES as a template; the oligonucleotide of SEQ ID NO. 12 having BamHI and NotI recognition sequences as a 5' primer; and the oligonucleotide of SEQ ID NO. 13 having StuI, ClaI and BglII recognition sequences as a 3' primer.

After the PCR product was cloned into the vector pCRII (Invitrogen, Calif., USA), the BamHI/BglII fragment was excised from the resulting vector and inserted into the BamHI site of MSN (KR Patent Application No. 1999-23398) in order to generate the plasmid MSN-IRES.

(6-2) Cloning of the MDR Gene and the Construction of Plasmid MTM

To generate an MDR gene fragment, PCR was performed using a plasmid containing MDR, which was obtained from Dr. Sugimoto (Cncer Chemotherapy center, Japanese Foundation for Cancer Research, Tokyo 170, Japan), as a template; the oligonucleotide of SEQ ID NO. 14 having BamHI and ClaI recognition sequences as a 5' primer; and the oligonucleotide of SEQ ID NO. 15 having SalI and BamHI recognition sequences as a 3' primer.

Figure 9:
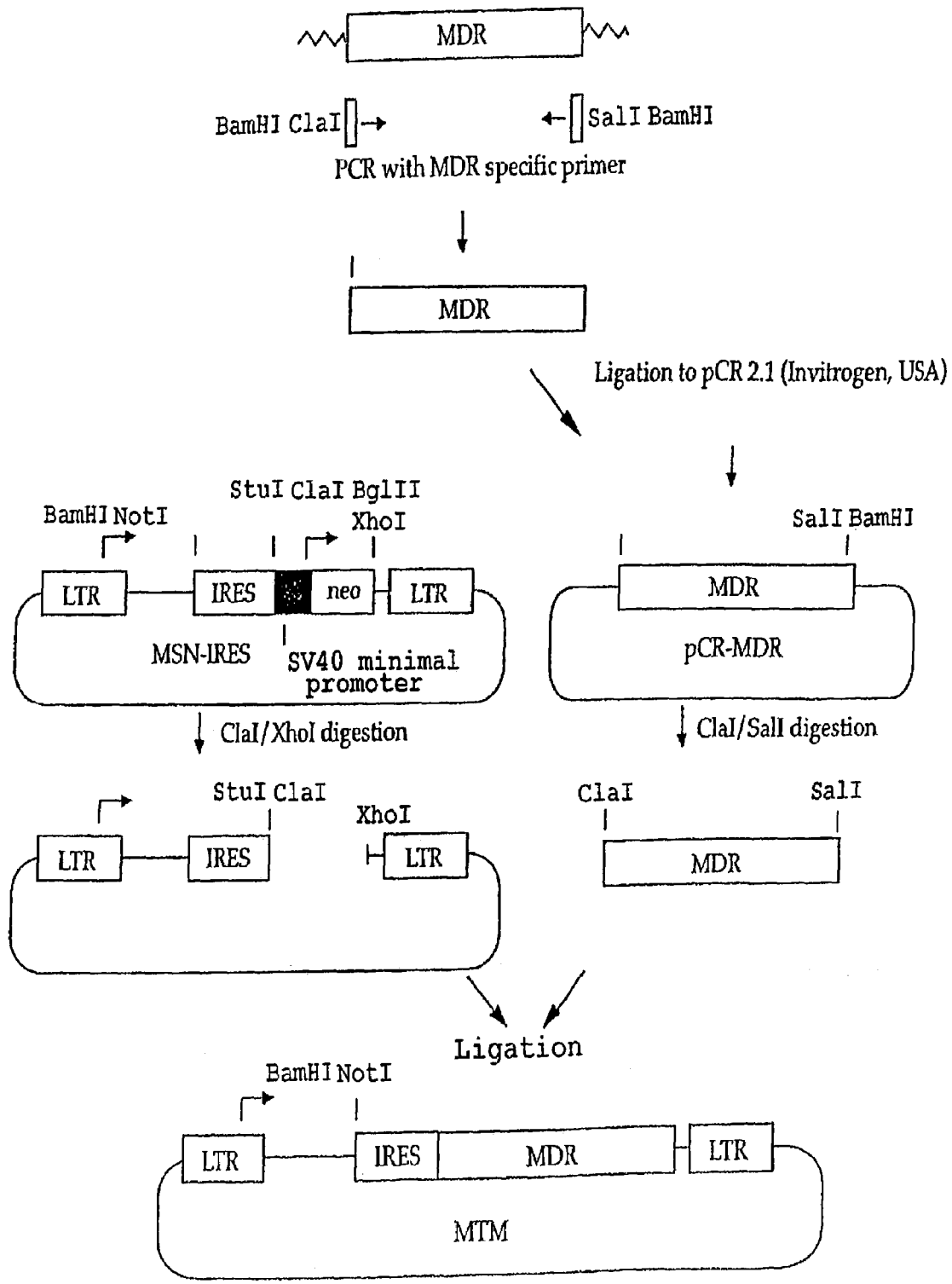
FIG. 9: the procedure for preparing the MTM vector which has an MDR gene as a selectable marker.

The PCR product was cloned into the vector pCRII (Invitrogen, Calif., USA) to generate pCR-MDR, and it was confirmed by sequencing analysis that the MDR gene was properly inserted. The BamHI/BglII fragment was excised from the pCR-MDR vector, and inserted into the plasmid MSN-IRES after the removal of the ClaI/XhoI fragment in order to generate the plasmid MTM (see FIG. 9).

(6-3) Construction of Vectors MTM4 and MTM5

Figure 10:
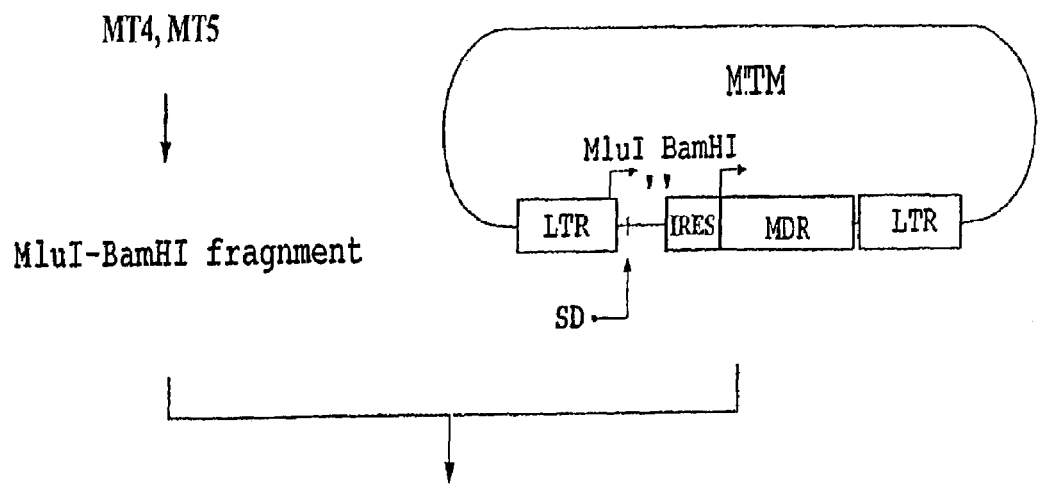
FIG. 10: the procedure for preparing vectors MTM4 and MTM5, each having an MDR gene as a selectable marker, and a modified EF1α non-coding sequence.
Figure 10:
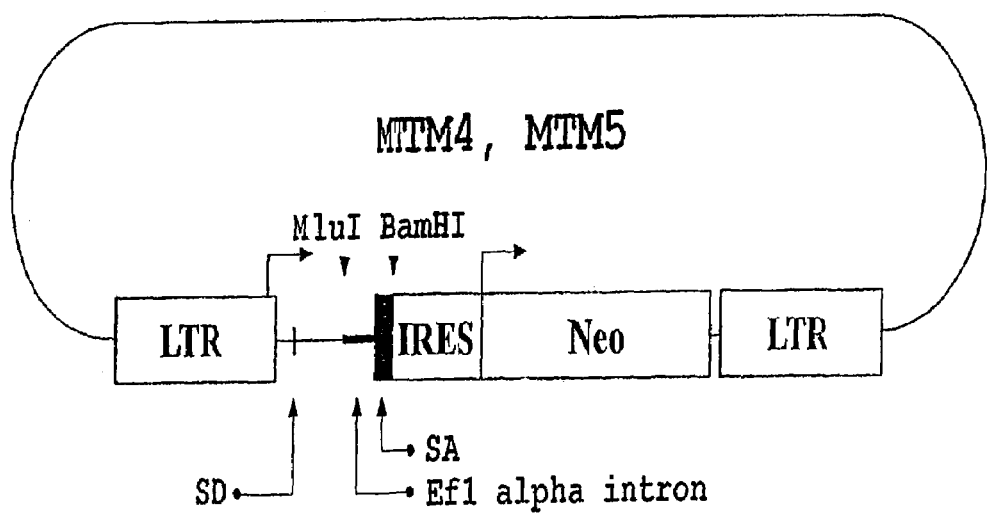

MluI/BamHI DNA fragments containing the modified non-coding sequence were obtained from vectors MT4 and MT5, respectively, and inserted into the MluI/BamHI site of MTM vector to construct plasmids MTM4 and MTM5, respectively (see FIG. 10). Therefore, the expression of the MDR gene from MTM4 and MTM5 is derived by the spliced mRNA.

Example 7

Efficiencies of MTM Vectors

To examine the efficiencies of vectors MTM, MTM4, and MTM5 obtained in Example 6, the IL-1ra gene was inserted into the BamHI sites of these vectors to generate vectors MTM-IL-1ra, MTM-IL-1ra, and MTM-IL-1ra, respectively. Each of the resulting vectors was transfected into 293T cells together with gag/pol, env expression vectors, the cells were incubated for 48 hours. The cell-free viral supernatants were used to transduce NIH3T3 cells, and incubated for 48 hours. IL-1ra activities of the transfected cells and the transduced cells were determined, and the viral titer was measured by counting the number of cells resistant to vincristine.

TABLE 9

| Vector | Relative IL-1ra activity | | |
|---|---|---|---|
| | Transfection | Transduction | Viral titer |
| MTM | 1.0 | 1.0 | 1.0 |
| MTM4 | 10.0 | 3.3 | 1.8 |
| MTM5 | 3.4 | 5.0 | 2.5 |

As can be seen in Table 9, the gene expression level of MTM5 is only about 30% of that for wild-type MTM4, but it is 3 folds higher than that of MTM. In addition, since the viral titer of MTM5 is much higher than those of MTM, and MTM4, MTM5 performs best in terms of the overall transductional efficiency.

To further compare the performance of retroviral vector in PG13 cells, each of the cell-free viral supernatant was used to transduce PG13 cells, and a virus producing cell line was obtained by selection with 25 ng/ml of vincristine for 2 weeks. The viral supernatant obtained from the PG13 producing cell line was used to transduce HT1080 cells, and IL-1ra activity and the viral productivity were measured.

TABLE 10

| Vector | Relative IL-1ra activity | Viral titer |
|---|---|---|
| MTM | 1.0 | 1.0 |
| MTM4 | 2.4 | 0.2 |
| MTM5 | 11.3 | 5.5 |

As the results in Table 10 shows, the viral titer of MTM5 is much higher than those of MTM, and MTM4, and thus, MTM5 has an excellent transductional efficiency.

As disclosed and verified above, the present invention provides an efficient and safe retroviral vector which can be advantageously used in gene therapy. The retroviral vector of the present invention has the following features:

1. Since all retroviral coding sequences (gag, pol and env gene sequences of MLV) are completely deleted, there is no possibility of replication-competent retrovirus being produced through homologous recombination.

2. Due to the presence of a heterologous intron, the splicing acceptor and/or non-coding sequence inserted upstream from the multi-cloning site, the foreign gene in the retroviral vector can be expressed efficiently.

3. Due to the introduction of a suitable mutation around the heterologous splicing acceptor, delicate balance between the splicing efficiency and viral titer can be maintained.

4. Since the U3 region of the 5' LTR is replaced with a heterologous promoter that promotes transcription, particularly in human cells, a human cell-derived packaging cell line transfected with the inventive vector exhibits a marked increase in viral titer.

5. An IRES or a heterologous promoter may be introduced in the inventive vector for the purpose of expressing two or more foreign genes. In this case, a minimal promoter may be inserted in order to minimize the interference by the heterologous internal promoter and also to clone a large-sized foreign gene.

What is claimed:

1. A retroviral vector comprising a nucleotide sequence between a 5' LTR and a 3' LTR, wherein said nucleotide sequence comprises
   a) a MLV minimal packaging sequence comprising a splicing donor,
   b) a poly-purine tract,
   c) a multi-cloning site, and
   d) a heterologous non-coding sequence comprising a splicing acceptor,
      wherein said heterologous non-coding sequence is located upstream of said multi-cloning site,
      wherein said heterologous non-coding sequence is the non-coding sequence of an EF1α, and
      with the exception that a region of the heterologous non-coding sequence downstream of said splicing acceptor comprises a mutated sequence.

2. The vector of claim 1, wherein said heterologous non-coding sequence is the sequence of the intron and exon 2 of a human EF1α, wherein the intron and exon 2 are located immediately upstream of the translation initiation codon of the human EF1α, with the exception that a region of said heterologous non-coding sequence downstream of said splicing acceptor comprises a mutated sequence.

3. The vector claim 1, wherein the vector further comprises one or more foreign genes.

4. The vector of claim 1, wherein said 5'LTR comprises a heterologous promoter.

5. The vector of claim 1, wherein the vector further comprises a first nucleotide sequence downstream of said multi-cloning site, wherein said first nucleotide sequence is a heterologous promoter.

6. The vector of claim 1, further comprising a nucleotide sequence encoding a selectable marker.

7. A mammalian host cell transformed with the vector of claim 1.

8. The vector of claim 1, wherein the vector is in a plasmid.

9. A cell comprising the vector of claim 1.

10. A composition comprising the vector of claim 1 and a suitable carrier.

11. The vector of claim 1, wherein the vector further comprises a first nucleotide sequence downstream of said multi-cloning site, wherein said first nucleotide sequence is an internal ribosome entry site.

12. The vector of claim 2, wherein said heterologous non-coding sequence is SEQ ID NO:1, with the exception that a region of said heterologous non-coding sequence downstream of said splicing acceptor comprises a mutated sequence.

13. The vector of claim 12, wherein said mutated sequence is at the 205th and 206th nucleotides of SEQ ID NO:1.

14. The vector of claim 13, wherein said mutated sequence is CC (cytosine-cytosine).

15. The vector of claim 3, wherein said foreign gene is a reporter gene.

16. The vector of claim 3, wherein said foreign gene is an IL-Ira gene.

17. The vector of claim 15, wherein said reporter gene is a luciferase gene.

18. The vector of claim 4, wherein said heterologous promoter is an HCMV IE promoter.

19. The vector of claim 5, wherein said heterologous promoter is an SV40 promoter.

20. The vector of claim 19, further comprising one or more foreign genes.

21. The vector of claim 6, wherein said selectable marker is a neomcyin resistance gene or a multi-drug resistance gene.

22. The mammalian host cell of claim 7, wherein said heterologous non-coding sequence is SEQ ID NO:1, with the exception that the 205th and 206th nucleotides of SEQ ID NO:1 are CC (cytosine-cytosine).

23. The vector of claim 8, wherein said heterologous non-coding sequence is SEQ ID NO:1, with the exception that the 205th and 206th nucleotides of SEQ ID NO:1 are CC (cytosine-cytosine).

24. A cell of claim 9, wherein the vector is in a plasmid.

25. The cell of claim 9, wherein the cell is a bacterial cell.

26. The cell of claim 9, wherein the cell is a packaging cell line.

27. A method of making infectious retroviral particles comprising cultivating the packaging cell line of claim 26 in a suitable medium, collecting the medium, and filtering the collected medium to obtain a cell-free viral supernatant.

28. A method of transducing mammalian cells comprising incubating the mammalian cells with the cell-free viral supernatant of claim 27.

29. The composition of claim 10, wherein said heterologous non-coding sequence is SEQ ID NO:1, with the exception that the 205th and 206th nucleotides of SEQ ID NO:1 are CC (cytosine-cytosine).

* * * * *